(12) United States Patent
Sasaki et al.

(10) Patent No.: US 10,578,430 B2
(45) Date of Patent: *Mar. 3, 2020

(54) EVALUATION METHOD OF ROAD SURFACE PROPERTY, AND EVALUATION DEVICE OF ROAD SURFACE PROPERTY

(71) Applicant: TOPCON CORPORATION, Tokyo (JP)

(72) Inventors: You Sasaki, Tokyo (JP); Kazuhiro Ogawa, Tokyo (JP); Tadayuki Ito, Tokyo (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/423,746

(22) Filed: Feb. 3, 2017

(65) Prior Publication Data

US 2017/0307369 A1 Oct. 26, 2017

(30) Foreign Application Priority Data

Feb. 4, 2016 (JP) .................. 2016-020248

(51) Int. Cl.
*G01B 11/30* (2006.01)
*G01N 21/88* (2006.01)
(Continued)

(52) U.S. Cl.
CPC ....... *G01B 11/306* (2013.01); *G01N 21/8851* (2013.01); *G06F 7/552* (2013.01); *G01N 2201/12* (2013.01); *H04N 7/183* (2013.01)

(58) Field of Classification Search
CPC .................................................. G01B 11/306
See application file for complete search history.

(56) References Cited

U.S. PATENT DOCUMENTS 5,130,709 A 7/1992 Toyama et al.
6,233,510 B1 5/2001 Platner et al.
(Continued)

FOREIGN PATENT DOCUMENTS

JP H10-288516 A 10/1998
JP 2010175756 A 8/2010
(Continued)

OTHER PUBLICATIONS

Fujiki et al., JP 2015-031018 (Machine translated English version).*

*Primary Examiner* — Hyun D Park
(74) *Attorney, Agent, or Firm* — Chiesa Shahinian & Giantomasi PC (57) ABSTRACT

To carry out evaluation of a road surface property easily and in a short period of time without being costly. Measurement data of a road surface measured for a predetermined road width along a path of a road to be measured is acquired; a unit area having a preset length dimension along the path in the road width is set along the path; a model plane in the unit area is set based on the measurement data at each point in the unit area; point group data is generated from a spaced amount of the model plane and each point in the unit area, visualize and display the spaced amount in the path, and display a result of evaluation obtained through statistical processing with the path shown on a map.

10 Claims, 10 Drawing Sheets

(51) Int. Cl.
*G06F 7/552* (2006.01)
*H04N 7/18* (2006.01)

(56) References Cited

U.S. PATENT DOCUMENTS

| | | |
|---|---|---|
| 2003/0069668 A1 | 4/2003 | Zurn |
| 2009/0295917 A1 | 12/2009 | Zhang et al. |
| 2009/0310143 A1 | 12/2009 | Gardiner et al. |
| 2010/0088024 A1* | 4/2010 | Takahara ............ B60W 40/072 701/532 |
| 2010/0182613 A1 | 7/2010 | Holton et al. |
| 2013/0103259 A1 | 4/2013 | Eng et al. |
| 2013/0266186 A1 | 10/2013 | Zhang et al. |
| 2014/0081573 A1 | 3/2014 | Urmson et al. |
| 2014/0104424 A1 | 4/2014 | Zhang et al. |
| 2014/0184800 A1 | 7/2014 | Hirai et al. |
| 2014/0355839 A1 | 12/2014 | Bridgers et al. |
| 2015/0169966 A1 | 6/2015 | Ishimaru et al. |
| 2015/0371095 A1 | 12/2015 | Hartmann et al. |
| 2016/0171278 A1* | 6/2016 | Ponder ............... G06K 9/00651 382/104 |

FOREIGN PATENT DOCUMENTS

| | | |
|---|---|---|
| JP | 2013205130 A | 10/2013 |
| JP | 204163707 A | 9/2014 |

* cited by examiner

EVALUATION METHOD OF ROAD SURFACE PROPERTY, AND EVALUATION DEVICE OF ROAD SURFACE PROPERTY

CROSS-REFERENCE TO RELATED APPLICATIONS

This application claims priority to Japanese Patent Application No. 2016-020248 filed on Feb. 4, 2016, which is incorporated herein by reference in its entirety.

TECHNICAL FIELD

The present invention relates to an evaluation method of a road surface property, and an evaluation device of the road surface property.

BACKGROUND OF THE INVENTION

Generally, roads produce splits and unevenness over time due to the passing of vehicles, and the like, and such splits and unevenness need to be repaired. In order to repair such roads, the road is inspected, and data on road surface property of the road, that is, data on a state of unevenness of the road surface are acquired. The data on the road surface property are acquired by measurement carried out by measuring personnel, or by causing a road surface property vehicle to travel along a predetermined path of a road to be measured. A device for irradiating a road surface with a scan light, and measuring a height of each point of the road surface is mounted on the road surface property vehicle.

Japanese Unexamined Patent Publication No. 10-288516 (hereinafter referred to as Patent document 1(A)) describes a device that projects light toward a plane while moving a moving body in a longitudinal direction of the plane, and measures a step difference of the plane according to the light projection result, the device having a configuration of including a means for detecting a moving distance, a light projecting means, a means for imaging a light irradiation line, a transverse direction data computing means for acquiring height data, a vertical direction data computing means, and a three-dimensional data computing means. According to such configuration, a technique in which the light is projected toward a plane RD from a moving body so that one irradiation line forms on the plane RD along a transverse direction W of the plane RD every time the moving body moves a predetermined distance, and an unevenness profile is acquired in real time by the various types of means is described.

However, causing the vehicle to travel on all lines of the road to be subjected to maintenance requires great trouble and time. Furthermore, since the road surface property vehicle is expensive, it is costly to carry out the measurement on all the lines.

SUMMARY OF THE INVENTION

In light of the foregoing, it is an object of the present invention to provide an evaluation method of a road surface property, and an evaluation device of the road surface property capable of evaluating the road surface property easily and in a short period of time without being costly.

An invention described in claim 1 for solving the problem described above relates to an evaluation method of a road surface property including the steps of acquiring measurement data on a spaced amount from a measurement reference plane of each point of a road surface measured for a predetermined road width along a path of a road to be measured; setting a unit area having a preset length dimension along the path in the road width along the path; setting a model plane in the unit area based on the measurement data at each point in the unit area; and generating point group data on a spaced amount of each point from the model plane in the unit area.

Similarly, according to the invention of claim 2, the evaluation method further includes a step of visualizing the point group data in the path.

According to the invention of claim 3, the evaluation method further includes a step of statistically processing the point group data for every unit area, and evaluating the road surface property.

According to the invention of claim 4, the evaluation method further includes a step of statistically processing the point group data for every unit area, and evaluating the road surface property.

According to the invention of claim 5, the model plane is calculated with a plurality of regions spaced apart in a direction of the road width in the unit area as a reference.

According to the invention of claim 1, the evaluation method further includes the steps of dividing the unit area into a plurality of sections and calculating a statistic of the point group data in each section; extracting a section having a statistic satisfying a predefined reference value; and assuming a section selected based on a changing amount of the statistic of the extracted section and a statistic of a section adjacent to the extracted section as a deformed area candidate.

An invention of claim 6 relates to an evaluation device of a road surface property, the evaluation device including a means that acquires measurement data on a spaced amount from a measurement reference plane of each point of a road surface measured for a predetermined road width along a path of a road to be measured; a means that sets a unit area having a preset length dimension along the path in the road width along the path; a means that sets a model plane in the unit area based on the measurement data at each point in the unit area; and a means that generates point group data on a spaced amount of each point from the model plane in the unit area.

According to the invention of claim 7, the evaluation device further includes a means that visualizes the point group data in the path.

According to the invention of claim 8, the evaluation device further includes a means that statistically processes the point group data for every unit area, and evaluates the road surface property.

According to the invention of claim 9, the evaluation device further includes a means that displays a result of evaluation obtained through statistical processing with the path shown on a map.

According to the invention of claim 10, wherein the model plane is calculated with a plurality of regions spaced apart in a direction of the road width in the unit area as a reference.

According to the invention of claim 6, the evaluation device further includes a means that divides the unit area into a plurality of sections and calculates a statistic of the point group data in each section; a means that extracts a section having a statistic satisfying a predefined reference value; and a means that assumes a section selected based on a changing amount of the statistic of the extracted section and a statistic of a section adjacent to the extracted section as a deformed area candidate.

According to the evaluation method of the road surface property and the evaluation device of the road surface property of the present invention, the evaluation of the road surface property can be carried out easily and in a short period of time without being costly.

In other words, according to the inventions described in claim 1 and claim 6, the measurement data of the road surface is acquired, the unit area having the preset length dimension along the path in a road width is set along the path, the model plane in the unit area is set based on the measurement data at each point in the unit area, and the point group data is generated. Thus, the property of the road surface can be accurately determined in accordance with the property of the road surface in the actual road surface.

According to the inventions described in claim 2 and claim 7, the point group data in the path is visualized, and thus the spaced amount of the road surface in the path can be intuitively grasped.

According to the inventions described in claim 3 and claim 8, the spaced amount is statistically processed for every unit area to evaluate the road surface property, and thus the road surface property for every unit area in a measured line can be acquired and the state of the road surface can be specifically grasped. Thus, when conducting a detailed inspection of the road surface property, a precise inspection can be carried out after grasping the state of the road surface.

According to the inventions described in claim 4 and claim 9, the result of the evaluation obtained through statistical processing is displayed with the path shown on a map, and hence the spaced amount of the road surface in the path can be intuitively grasped on the map.

According to the inventions described in claim 5 and claim 10, calculation is carried out with a plurality of areas spaced apart in a direction of the road width in the road surface as a reference, and hence a variety of measurement conditions can be responded by appropriately selecting two reference areas.

According to the inventions described in claim 1 and claim 6, the unit area is divided into a plurality of sections, a statistic of the point group data in each section is calculated, a section having a statistic satisfying a predefined reference value is extracted, and a section detected based on a changing amount of the statistic of the extracted section and a statistic of a section adjacent to the extracted section is detected as a deformed area candidate to become a recess candidate or a projection candidate, so that a recess formed area of a pot hole, and the like or a projection formed area of a protrusion formed between splits, and properties of such areas can be automatically detected.

DETAILED DESCRIPTION OF THE EXEMPLARY EMBODIMENTS

An evaluation method of a road surface property, and an evaluation device of the road surface property according to a mode for carrying out the present invention will be described.

An evaluation method of a road surface property and an evaluation device of the road surface property according to an embodiment of the present invention entirely evaluate measurement data on a spaced amount (height) from a measurement reference plane at a road surface acquired by a road surface measuring device as a plane, which configures an MMS (Mobile Mapping System), and carry out evaluation of the road surface property. The road surface measuring device is mounted on a travelling vehicle, and acquires highly accurate actual measurement data by scanner and image. Specifically, in each target unit area (e.g., 2 m×3 m (e.g., lane width)) along a vehicle travelling line, a model plane is set using a point group in a region having a predetermined width dimension and where vehicle does not travel and hence hollowing is not anticipated, for example, a line end. The two regions used for such setting are not limited to both ends. In addition, the vicinity of the center of a vehicle width, and a paint of a lane mark can be used.

Point group data, which is a spaced amount from the model plane, is calculated for all points within the target unit area. The spaced amounts at all points are statistically processed in the unit area and RMS (Root Mean Square) is calculated as a statistic to obtain a representative value representing each unit area as an evaluation value. In acquiring the measurement data, the orientation of the vehicle at the time of the measurement is taken into consideration in the road surface measuring device, and hence area discrimination along the travelling line, and the like can be automatically carried out without requiring human determinations and operations. Furthermore, the lane mark used for the two regions described above can be extracted by measuring the luminance of the road surface at the time of the measurement. Moreover, a curb portion at both ends of the road can be extracted with a normal line of the road surface, a lower (low elevation) edge of the curb region at both ends of the road can be acquired, and a plane can be determined to include the edge at both ends of the road. A precise measurement is carried out on the basis of information on the road surface property acquired in the above manner.

Figure 1:
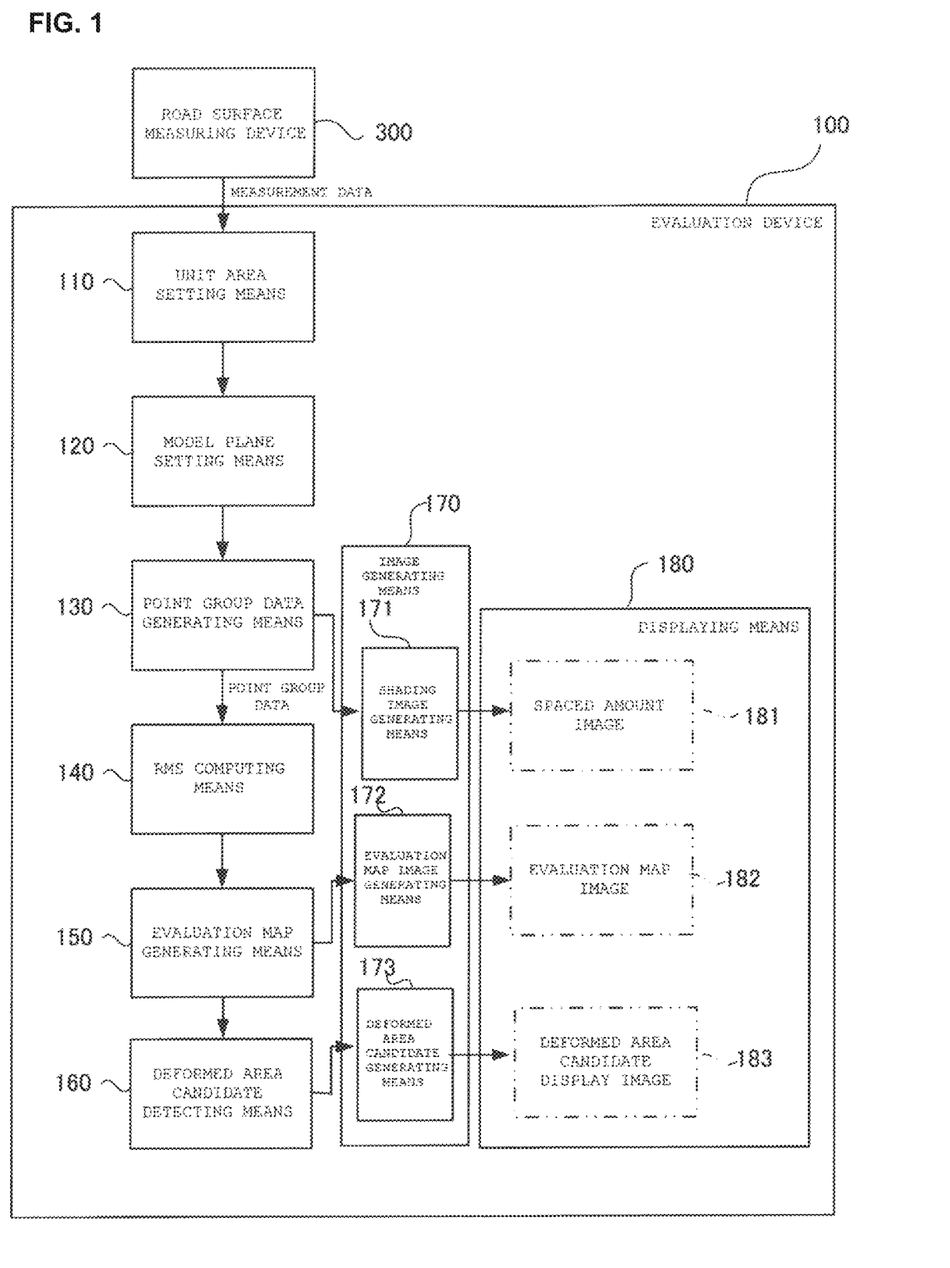
FIG. 1 is a block diagram showing a configuration of an evaluation device of a road surface property according to an embodiment of the present invention.
Figure 2:
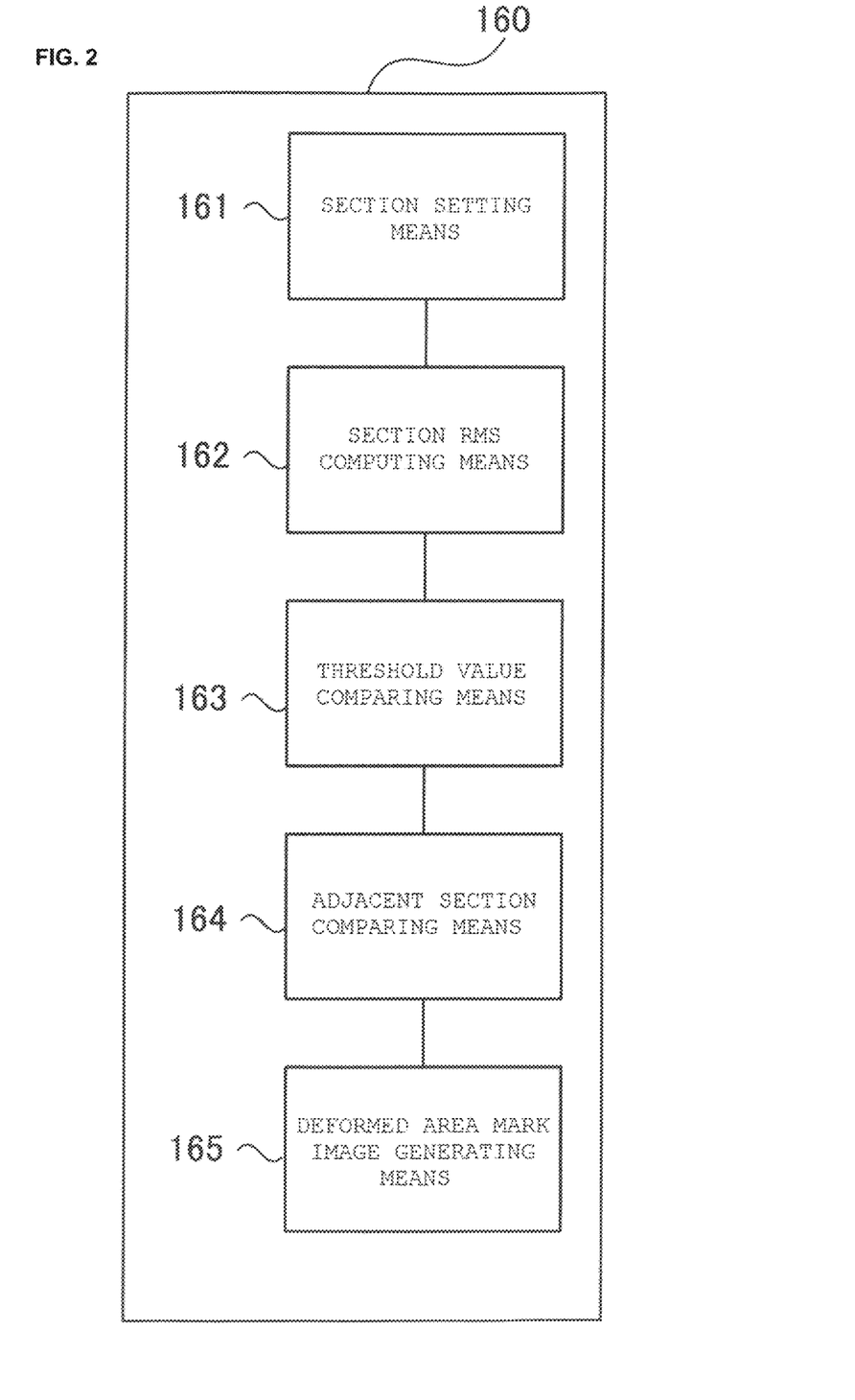
FIG. 2 is a block diagram showing a deformed area candidate detecting means.

The evaluation device of the road surface property will be described below. FIG. 1 is a block diagram showing a configuration of an evaluation device of a road surface property according to an embodiment of the present invention, and FIG. 2 is a block diagram showing a deformed area candidate detecting means.

An evaluation device 100 of the road surface property according to an embodiment of the present invention generates point group data based on a measurement result of a road surface measuring device 300, and carries out evaluation of the road surface property and generation of recess candidate images.

The road surface measuring device 300 is known. The road surface property can be evaluated at substantially the same time as the scanning of the road surface if the evaluation device 100 is mounted on a vehicle along with the road surface measuring device 300.

Figure 3A:
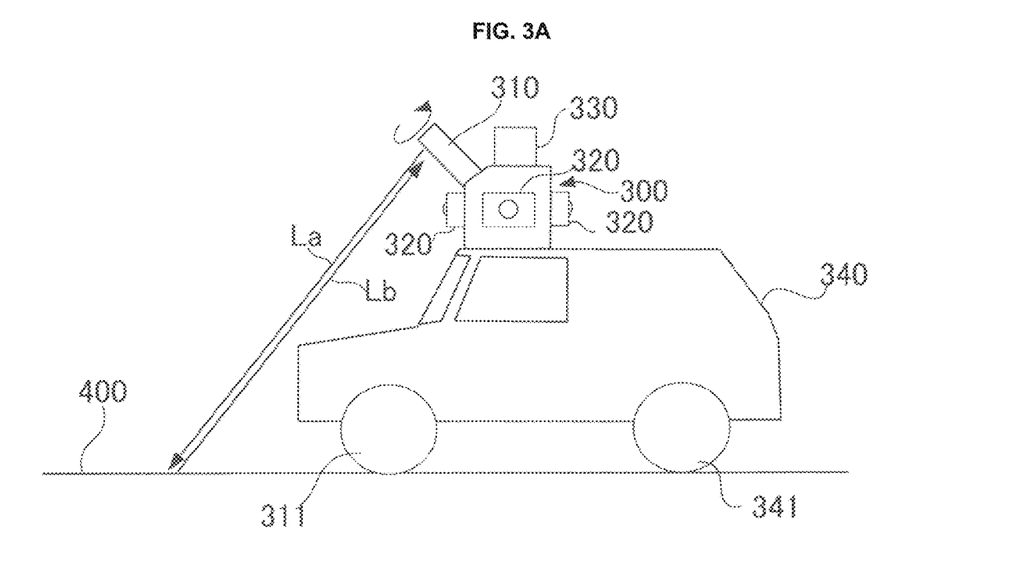
FIG. 3A is a side view and FIG. 3B is a plan view showing a measurement state of a road surface by a data acquiring device.
Figure 3B:
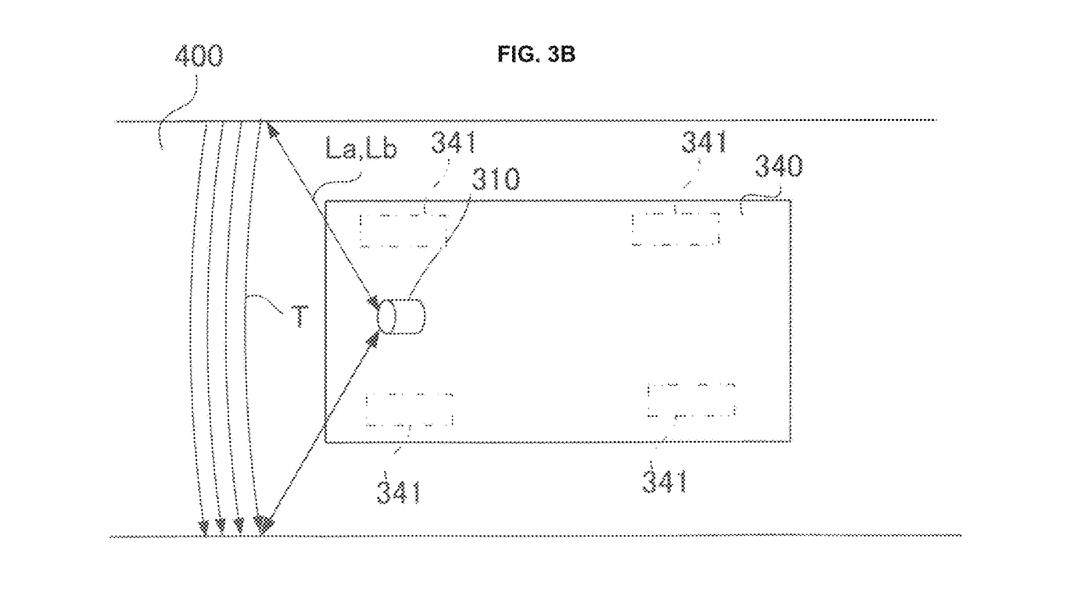

FIG. 3A is a side view and FIG. 3B is a plan view showing a measurement state of the road surface by the road surface measuring device. As shown in FIG. 3A, the road surface measuring device 300 is mounted on a vehicle 340 travelling on a road 400. The road surface measuring device 300 includes a scanner 310, a whole circumference camera 320, a laser pointer 330, an GNSS (Global Navigation Satellite System) device, an orientation detecting device of the road surface measuring device 300, an acceleration meter, and the like. The road surface measuring device 300 irradiates a scan light La in a spiral form toward a diagonally front side of the vehicle 340 with the scanner 310 while acquiring the position with the GNSS device, and receives a reflected light Lb from the road 400. The measurement data of the road 400 is acquired based on a time until the reception. Thus, a trajectory T of the scan light La at the road 400 becomes an arcuate shape, as shown in FIG. 3B.

At the same time, the road surface measuring device 300 acquires an image of a road over the entire circumference with the whole circumference camera 320. The laser pointer 330 scans and irradiates the road surface with a visible laser, and projects and displays a recess mark, to be described later, at a periphery of a recess candidate of the road surface as a recess detection mark.

Figure 4A:
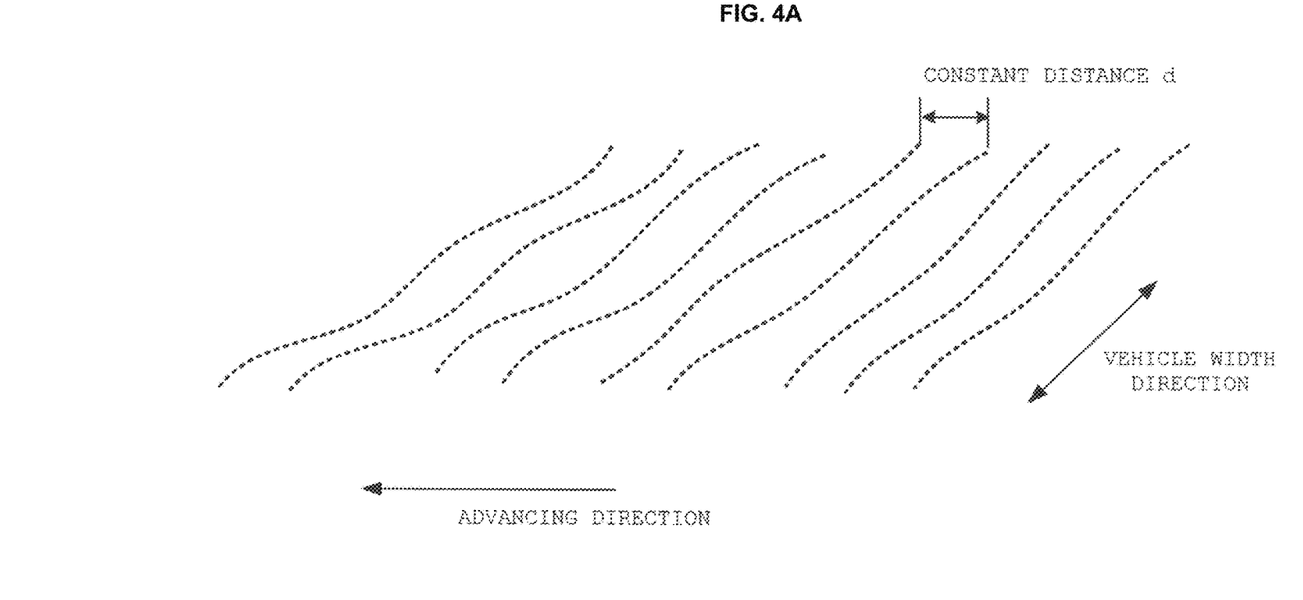
FIG. 4A is a perspective view of measurement data.
Figure 4B:
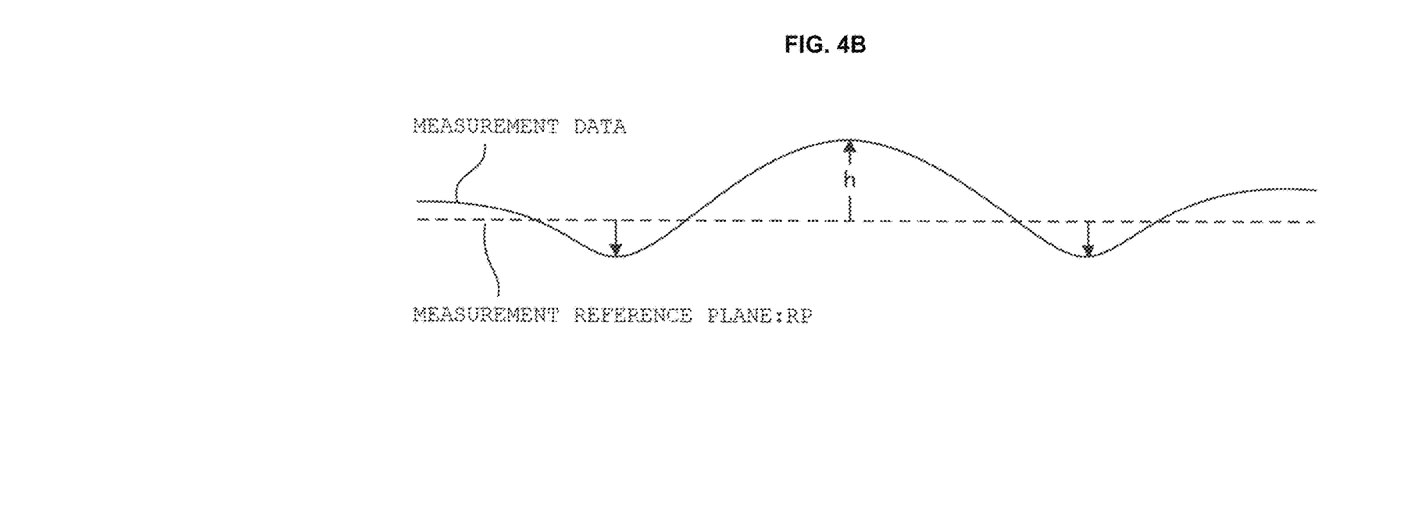
FIG. 4B is a schematic view showing the measurement data and a measurement reference plane.

FIG. 4A is a perspective view of measurement data, and FIG. 4B is a schematic view showing the measurement data and a measurement reference plane. The road surface measuring device 300 is mounted with the GNSS device for acquiring its position, the orientation detecting device of the road surface measuring device 300, the acceleration meter, and the like, where the measurement data of each point on a plurality of trajectories of the scan light La respectively spaced apart by a constant distance "d" in the road 400 is acquired, as shown in FIG. 4A. As shown in FIG. 4B, the measurement data represents a spaced amount "h" from a measurement reference plane (e.g., geoid plane) RP set by the road surface measuring device 300.

As shown in FIG. 1, the evaluation device 100 acquires the measurement data from the road surface measuring device 300, and generates the point group data and evaluates the road surface property. The evaluation device 100 includes a unit area setting means 110, a model plane calculating means 120, a point group data generating means 130, an RMS computing means 140, an evaluation map generating means 150, a deformed area candidate detecting means 160, an image generating means 170, and a displaying means 180.

The evaluation device 100 is configured as a computer equipped with a CPU (Central Processing Unit) for a processing device, a RAM (Random Access Memory) for a main storage device, a ROM (Read Only Memory), an HDD (Hard Disc Drive) for an auxiliary storage device, and the like, and realizes the functions of the unit area setting means 110, the model plane calculating means 120, the point group data generating means 130, the evaluation map generating means 150, the deformed area candidate detecting means 160, and the image generating means 170 by executing a program with the CPU.

Figure 5A:
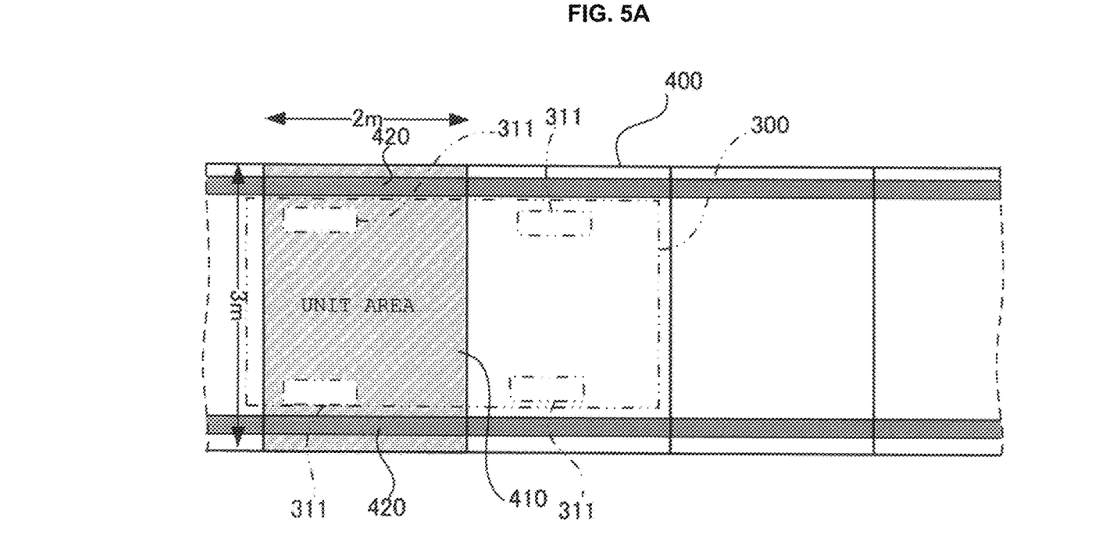
FIG. 5A is a schematic view showing a unit area of an acquired state of point group data.
Figure 5B:
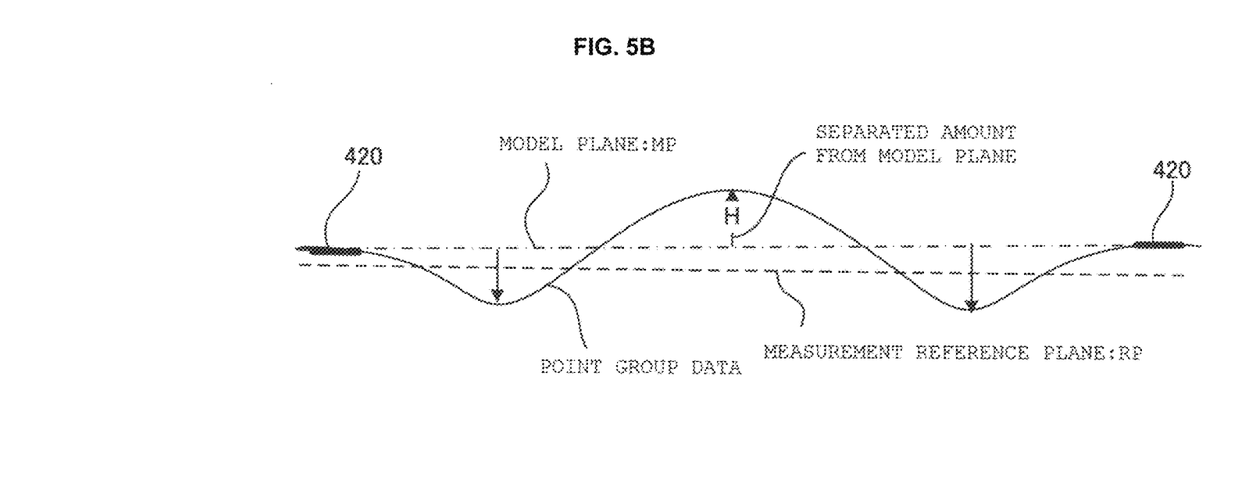
FIG. 5B is a schematic view showing the point group data and a model plane MP.

The unit area setting means 110 sets a unit area having a preset length dimension along the path in a width of a road along the relevant path. FIG. 5A is a schematic view showing a unit area of an acquired state of point group data and FIG. 5B is a schematic view showing the point group data and the model plane MP. The unit area setting means 110 divides the road 400 to be measured to, for example, a unit area 410 having a width of 3 m and a length of 2 m, as shown in FIG. 5A. A width dimension can be set with the width of one lane of the road, from one road shoulder to another shoulder, the width, and the like of the vehicle used for the measurement, and the like as a reference. The length dimension is not limited to 2 m and can be appropriately set, but the computation of the setting of the model plane MP, and the like become cumbersome, and the gap between the model plane MP and the road surface shape may become large if the length dimension is too long.

The model plane calculating means 120 sets the model plane MP in the unit area 410 based on the measurement data, which is the spaced amount from the measurement reference plane, of each point at the measurement point in the unit area 410. The model plane MP is set based on a plurality of, two in the present example, regions spaced apart in the road width direction, for example, a reference region 420, which is a region having a width of 20 cm spaced apart by a predetermined distance (e.g., 20 cm) to the outer side from a wheel 341 of the vehicle 340, as shown in FIG. 4A. Specifically, the model plane can be obtained through a least square method from a great number of point groups belonging to the reference region 420. The reference region is not limited to two, and may be three or more such as three regions of a central region and regions on both end sides. In addition to the example above, the point group in a region having an interval dimension and a width dimension of a certain extent, and where damages and hollowing by the travelling of the vehicle are not anticipated, for example, the line end, the vicinity of the center of the vehicle width, and the paint of the lane mark can be used for the reference region. The lane mark can be acquired by measuring the luminance of the road surface at the time of the measurement by the road surface measuring device 300.

Figure 6:
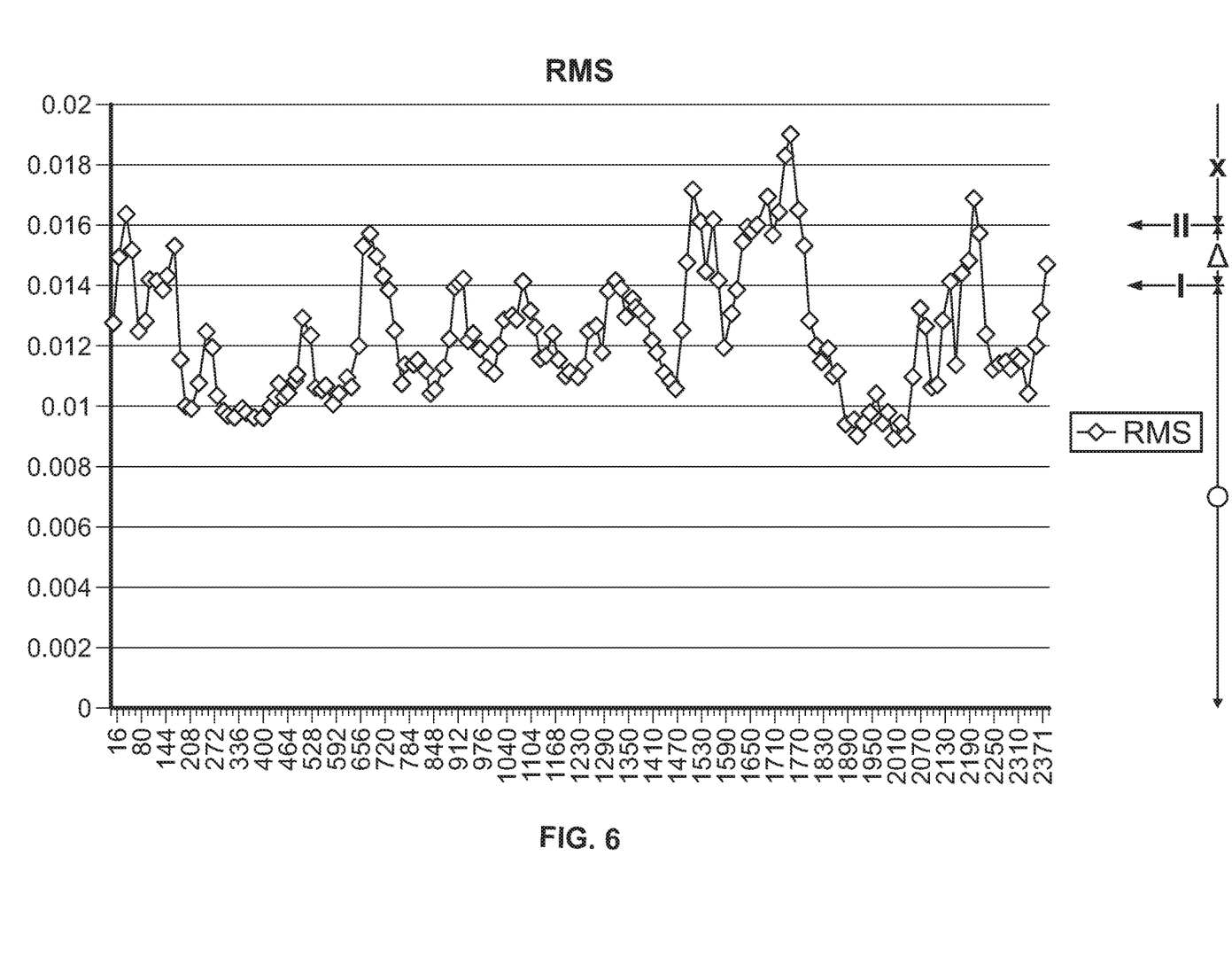
FIG. 6 is a graph showing change in RMS value in a measuring path.

As shown in FIG. 6, the point group data generating means 130 calculates a spaced amount "H" between the model plane MP and each point. The point group data is thereby generated from the spaced amount of each point in the unit area 410.

The RMS computing means 140 calculates the RMS (Root Mean Square), which is the statistic, in each unit area from the point group data obtained by the point group data generating means 130 in each unit area 410. FIG. 6 is a graph showing change in the RMS value in the measuring path. The RMS value of each unit region is shown on a vertical axis, and a distance is shown on a horizontal axis. Other than the RMS, other statistics can be used. The distribution of the road surface property in the path thus can be known.

The evaluation map generating means 150 evaluates the road surface property for each position of the road based on the RMS value obtained by the RMS computing means 140, and allocates the evaluation result to the roads on the map. In other words, in order to evaluate the road surface property from the RMS value shown in FIG. 6, for example, two values, value I and value II (I<II), are set. Determination is made that the road surface property is satisfactory "○" if smaller than value I, the road surface property is normal "Δ" if greater than or equal to value I and smaller than value II, and the road surface property is poor "x" if greater than or equal to value II. The evaluation result can be displayed on a map displaying the measured path.

Figure 9A:
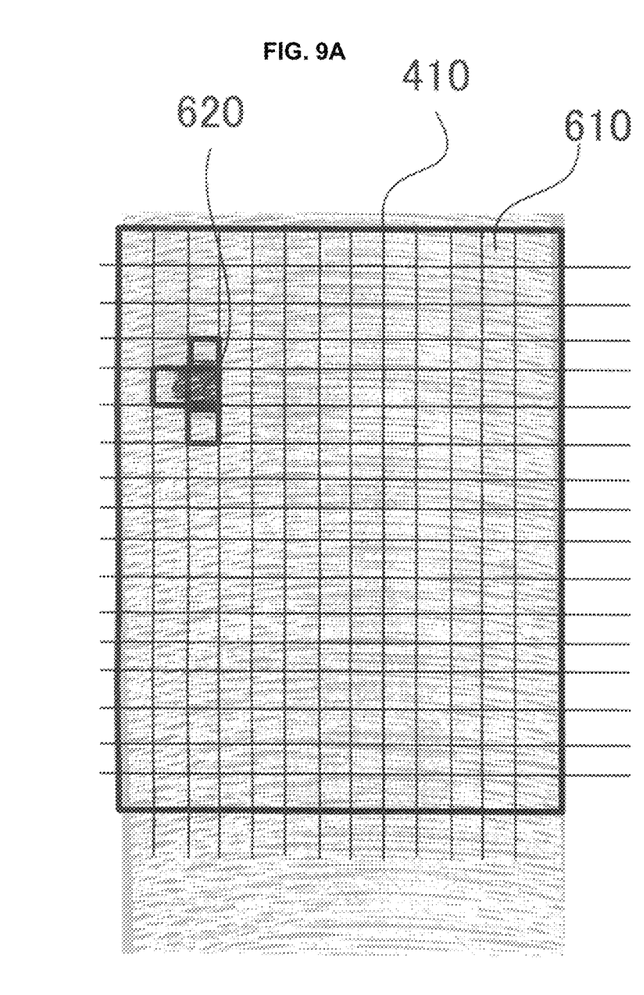
FIG. 9A is a schematic view showing a section in a unit area of a deformed area candidate.
Figure 9B:
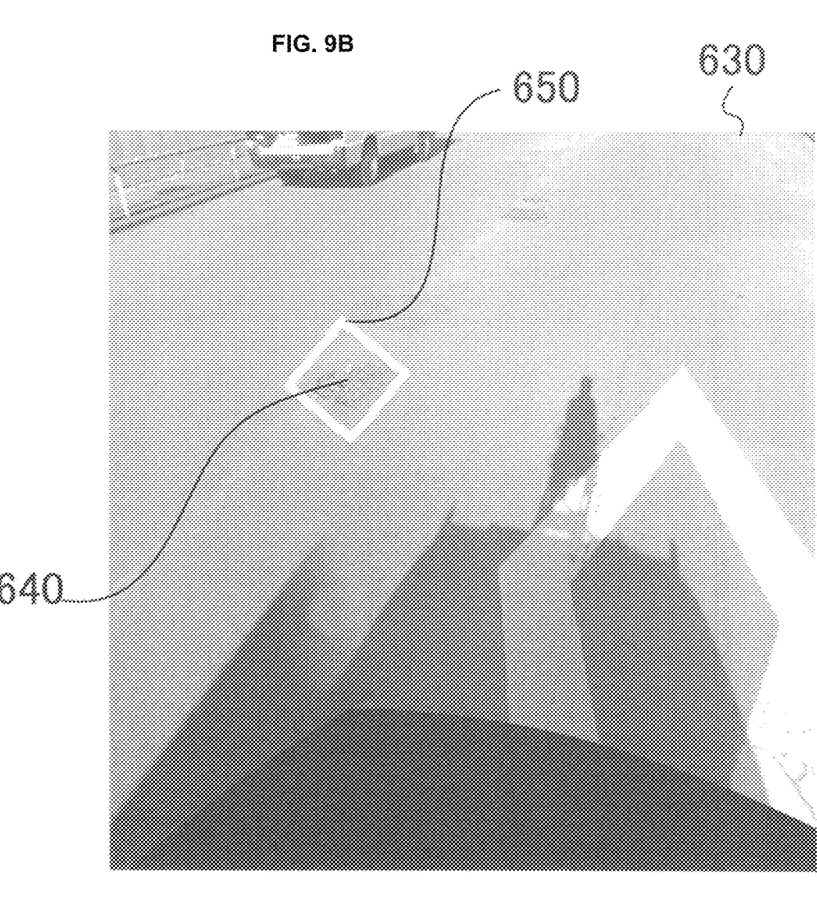
FIG. 9B is a view showing a display of a deformed area mark on a road surface by a laser pointer.

The deformed area candidate detecting means 160 will now be described. As shown in FIG. 2, the deformed area candidate detecting means 160 includes a section setting means 161, a section RMS computing means 162, a threshold value comparing means 163, an adjacent section comparing means 164, and a deformed area detection mark generating means 165. FIG. 9A is a schematic view showing a section in the unit area of a deformed area candidate, and FIG. 9B is a view showing a mark display on a road surface by a laser pointer.

First, the section setting means 161 divides the unit area 410 into a plurality of sections 610, 610, . . . , 610. As shown in FIG. 9A, the unit area 410 is marked to a grid form to be divided into regularly arranged sections 610, 610, . . . , 610.

Figure 10A:
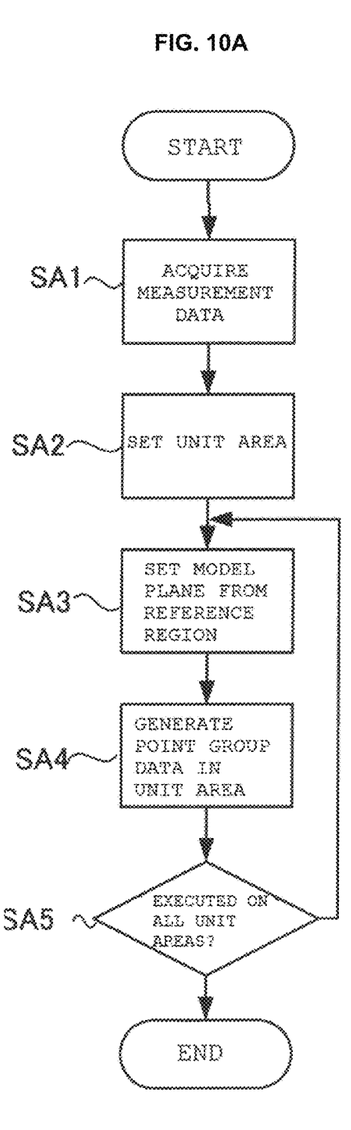
FIGS. 10A-C is a flowchart showing processes of the evaluation device of the road surface property.
Figure 10B:
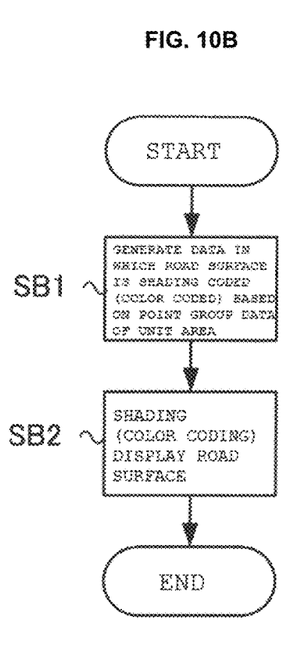

The section RMS computing means 162 calculates the RMS (Root Mean Square) as the statistic of the point group data belonging to each section as a representative value of each section (step SB2 of FIG. 10B). The threshold value comparing means 163 compares the representative value of each section with a predefined reference value to extract a section satisfying the reference value.

Next, the adjacent section comparing means 164 compares the extracted representative value of each section and the representative value of the adjacent section, and compares the difference with a predefined threshold value to detect a deformed area candidate. In other words, an area where an absolute value of the difference with the adjacent section is greater than the threshold value is selected as a deformed area candidate. A recess candidate or a projection candidate can be discriminated by the representative value and a sign of the difference of the representative values. Determination is made as the deformed area candidate even if the sections having a changing amount greater than the threshold value are adjacent to each other. The recess candidate includes a pot hole, and the like, and the projection candidate includes a protrusion, and the like formed between the splits.

The image generating means 170 includes a shading image generating means 171, an evaluation map image generating means 172, and a deformed area candidate image generating means 173. The shading image generating means 171 generates shading image data of the road surface based on the spaced amount from the model plane MP generated by the point group data generating means 130. The shading image allows the splits and the uneven state of the road to be visible on the image of the road.

The evaluation map image generating means 172 generates a map image displaying the evaluation of the road surface property based on the map data generated by the evaluation map generating means 150. According to such map image, the evaluation of the road surface property at each point of the road displayed on the map is additionally stated, and thus can be easily recognized.

The deformed area candidate image generating means 173 generates a deformed area detection mark as an area corresponding to the contour of the section to become the recess candidate from the detection result of the deformed area candidate detecting means 160. A deformed area detection mark 650 created at a periphery of the recess candidate image 640 of the road image 630 is thereby displayed, as shown in FIG. 9B. In the example shown in FIG. 9A, a pot hole, which is a recess, is shown as a deformed area. When the vehicle 340 mounted with the road surface measuring device 300 arrives near the recess candidate, the deformed area of the road surface can be irradiated and pointed out with the laser pointer 330. The projection can be similarly pointed out.

The displaying means 180 displays a spaced amount image 181 based on the shading image data from the shading image generating means 171, an evaluation map 182 based on the map data from the evaluation map image generating means 172, and a recess candidate display image 183 based on the recess detection mark from the deformed area candidate image generating means 173.

Figure 7A:
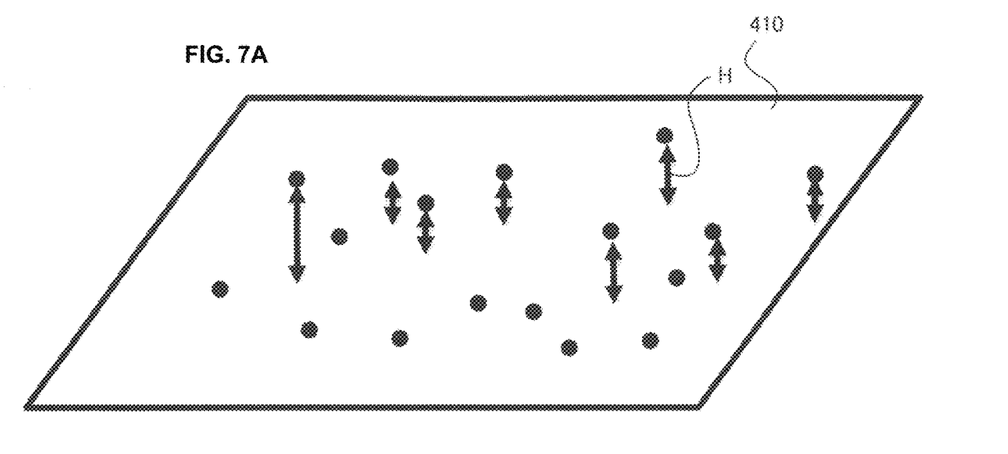
FIG. 7A is a perspective schematic view showing the model plane MP and the point group data of a spaced amount image.
Figure 7B:
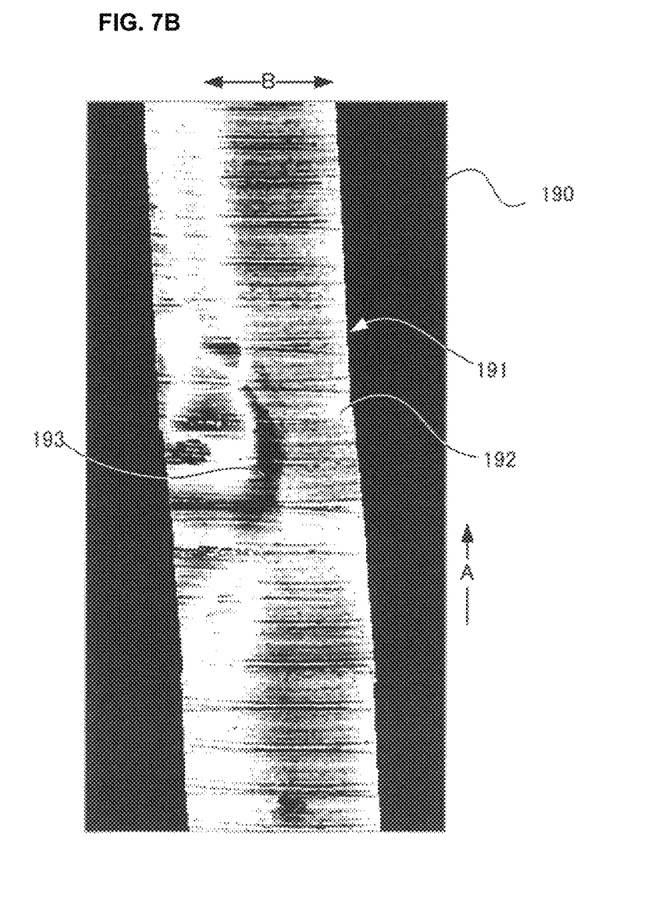
FIG. 7B is a view showing the spaced amount image.

The spaced amount image 181 will now be described. FIG. 7A is a perspective schematic view showing the model plane MP and the point group data associated with a spaced amount image, and FIG. 7B is a view showing the spaced amount image. As shown in FIG. 7A, based on the spaced amount (H) from the model plane MP at each point of the unit area 410, the shading color coding display of the road based on the spaced amount of each point of the road 191 is carried out in the spaced amount image 190, as shown in FIG. 7B. An arrow A in the figure indicates an advancing direction of a measuring vehicle, and an arrow B indicates a road width direction of the road 191. The spaced amount image 190 shown in FIG. 7B is displayed in grayscale, where an area 192 higher than the model plane MP of the road 191 is displayed in white, an area 193 lower than the model plane MP is displayed in black, and an area in between is displayed in gray shading. The spaced amount from the model plane MP in the road thus can be easily recognized. Furthermore, such image can be assumed as a color image in which the high and low state can be more easily recognized.

Figure 8:
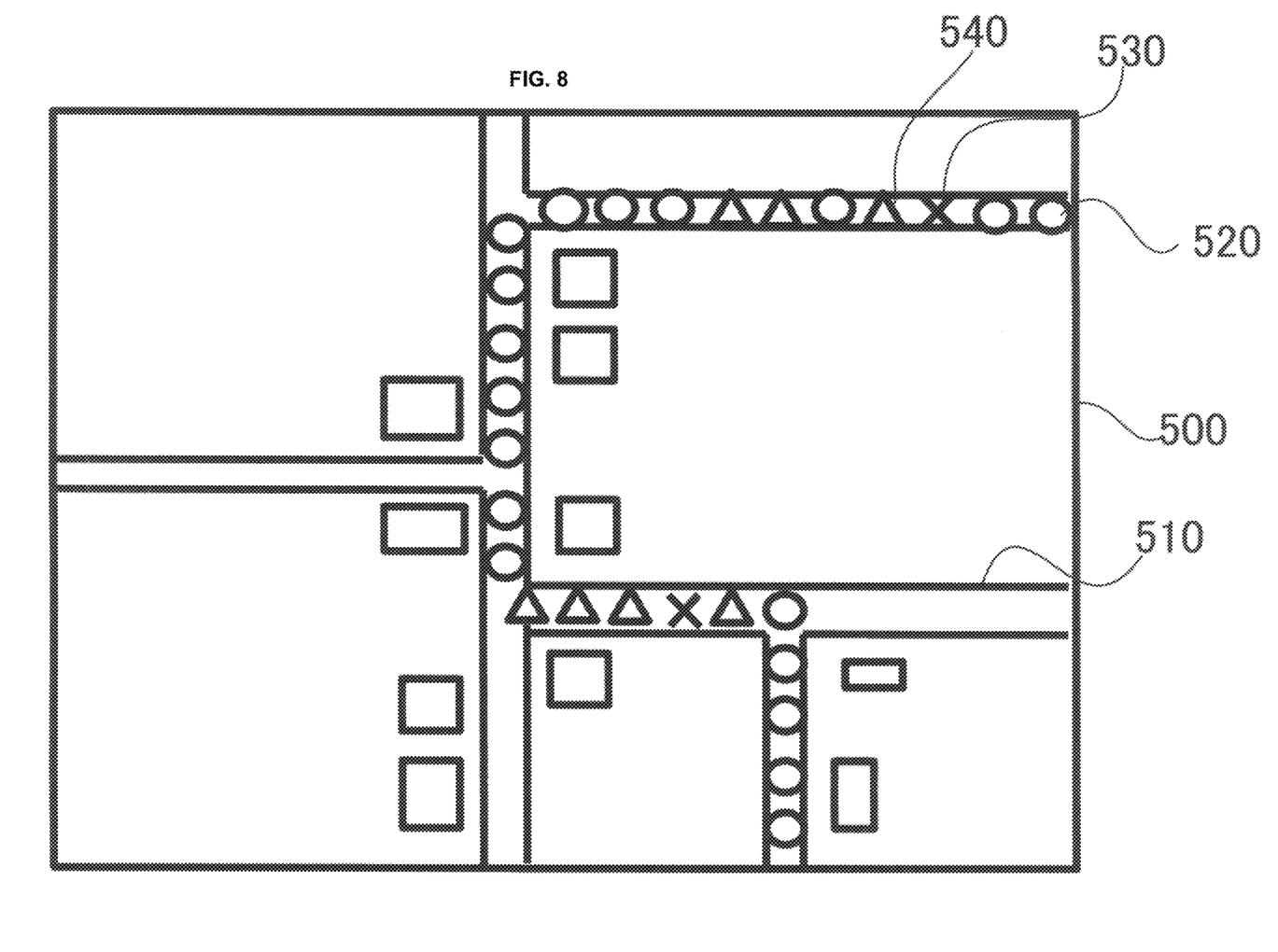
FIG. 8 is a schematic view showing an evaluation map.

The evaluation map 182 will now be described. FIG. 8 is a schematic view showing an evaluation map. The map data generated by the evaluation map generating means 150 is made visible by the evaluation map image generating means 172 of the image generating means 170, and displayed as the evaluation map 182 on the displaying means 180. A "○" display 520 indicating satisfactory road surface property, "Δ" display 530 indicating normal road surface property, and "x" display 540 indicating poor road surface property are made on the road 510 displayed on the map screen 500. Thus, the evaluation result of the road surface property thus can be recognized on the map in one glance.

The evaluation device 100 is mounted on the vehicle 340 mounted with the road surface measuring device 300, and can display the spaced amount image 181 and the evaluation map 182 immediately after acquiring the data based on the result acquired by the road surface measuring device 300.

Figure 10C:
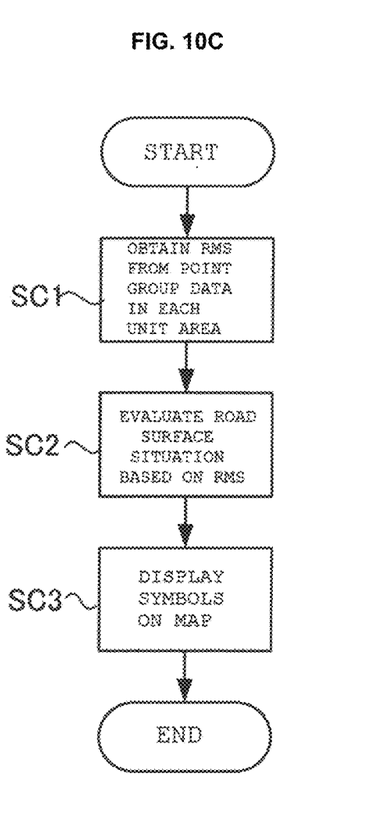

The flow of processes in the evaluation device 100 will now be described. FIGS. 10A-C is a flowchart showing processes of the evaluation device of the road surface property. First, a process of obtaining the spaced amount from the model plane MP at each point in the unit area will be described based on FIG. 10A. The unit area setting means 110 of the evaluation device 100 acquires the measurement data of the road surface from the road surface measuring device 300 (SA1). The measurement data is acquired by the road surface measuring device 300 described above. The road surface measuring device 300 can acquire the measurement data of the road 400 even if the vehicle 340 is travelling at high speed. Thus, the data can be acquired at high speed.

Next, the unit area setting means 110 cuts out the unit area (SA2). The model plane calculating means 120 then sets the model plane in the unit area based on each reference region 420 (SA3). Furthermore, the point group data generating means 130 calculates the spaced amount (H) from the model plane calculating means 120 of each point in the unit area to generate the point group data (SA4). Such processes are executed for all the unit areas (SA5).

A process of displaying the spaced amount image 181 of the road on the displaying means 180 will now be described based on FIG. 10B. The shading image generating means 171 of the image generating means 170 generates image data in which the road surface image is a shading coded (color coded) based on the point group data of each unit area from the point group data generating means 130 (SB1). The displaying means 180 then displays the spaced amount image 181 of the road based on the image data (SB2). The splits and uneven state of the road are thereby displayed.

Furthermore, the display process of the evaluation map 182 will be described next based on FIG. 10C. The RMS computing means 140 obtains the RMS value of the point group data of each unit area in each unit area (SC1). Next, the evaluation map generating means 150 evaluates the road surface situation based on the RMS value of each unit area and sets the same on the road of the map (SC2). The evaluation map image generating means 172 generates the evaluation map image and displays the evaluation map 182 on the displaying means 180 (SC3). The evaluation of the road surface property is thereby displayed on the road of the map.

As described above, according to the embodiment of the present invention, the spaced amount (point group data) from the model plane MP at each point corresponds to the hollowed amount or the raised amount at the relevant location, and thus the state of the road can be evaluated without being subjected to the influence of water drainage gradient, and the like of the road. Furthermore, the entire evaluation including the vehicle width direction and the travelling direction can be carried out, and whether a split or simply a hole can be easily determined. A linear model is conventionally used for the evaluation of the hollowed amount in the evaluation only in the vehicle width direction, but in such a case, the linear model is greatly influenced by erroneous factors such as grass along the road, whereas, in the present embodiment, the model plane is not greatly influenced by a few erroneous factors, and a reliable evaluation can be made.

In the present embodiment, a normal line of each point is obtained and set as a threshold value, thus enabling noise removal. The road surface measuring device can also acquire time information, and thus can give the time information to the measurement value to carry out evaluation and management. In addition to being able to efficiently carry out the evaluation at uniform evaluation criteria, real time process also can be carried out since the data is automatically processed without human assistance after the acquisition of the data. Furthermore, the evaluation of each area can be simply represented with "○", "Δ", and "x", which can be used to carry out simple examinations. Moreover, the spaced amount from the model plane MP can be displayed by color coding, shading, and the like on the map, and the overall situation can be easily grasped at one glance. Furthermore, in the present embodiment, the formed areas of the recess and the projection, as well as the properties thereof can be automatically detected since the recess candidate is detected and the recess detection mark is displayed.

The invention claimed is:

1. An evaluation method of a road surface property comprising the steps of:

scanning a road surface to obtain measurement data based on reflected scan light;
acquiring the measurement data on a spaced amount from a measurement reference plane of each point of the road surface measured for a predetermined road width along a path of a road to be measured;
setting a unit area having a preset length dimension along the path in the predetermined road width along the path;
setting a model plane in the unit area based on the measurement data at each point in the unit area;
generating point group data on a spaced amount of each point from the model plane in the unit area including:
dividing the unit area into a plurality of sections and calculating a first Root Mean Square (RMS) statistic of the point group data in each section thereby obtaining a representative value representing each unit area as an evaluation value;
extracting a section having in which a second RMS statistic satisfies a predefined reference value; and
assuming a section selected based on a changing amount of the second RMS statistic of the extracted section and a third RMS statistic associated with a section adjacent to the extracted section as a deformed area candidate; and
evaluating the road surface property using the point group data generated and identifying at least one recess candidate associated with the road.

2. The evaluation method of the road surface property according to claim 1, further comprising a step of visualizing the point group data in the path.

3. The evaluation method of the road surface property according to claim 2, further comprising a step of statistically processing the point group data for every unit area, for the evaluating the road surface property.

4. The evaluation method of the road surface property according to claim 3, further comprising a step of displaying a result of evaluation obtained through statistical processing with the path shown on a map.

5. The evaluation method of the road surface property according to claim 1, wherein the model plane is calculated with a plurality of regions spaced apart in a direction of the predetermined road width in the unit area as a reference.

6. An evaluation device of a road surface property comprising:

a scanner that obtains measurement data of a road surface based on reflected scan light;
a unit area setting means that acquires the measurement data on a spaced amount from a measurement reference plane of each point of the road surface measured for a predetermined road width along a path of a road to be measured, sets a unit area having a preset length dimension along the path in the predetermined road width along the path;
a model plane setting means that sets a model plane in the unit area based on the measurement data at each point in the unit area;
a point group data generating means that generates point group data on a spaced amount of each point from the model plane in the unit area including:
dividing the unit area into a plurality of sections and calculating a first Root Mean Square (RMS) statistic of the point group data in each section thereby obtaining a representative value representing each unit area as an evaluation value;
extracting a section having in which a second RMS statistic satisfies a predefined reference value; and assuming a section selected based on a changing amount of the second RMS statistic of the extracted section and a third RMS statistic associated with a section adjacent to the extracted section as a deformed area candidate; and an evaluation map generating means for evaluating the road surface property using the point group data generated and identifying at least one recess candidate associated with the road for use in repairing the road.

7. The evaluation device of the road surface property according to claim 6, further comprising an image generating means for visualizing the point group data in the path.

8. The evaluation device of the road surface property according to claim 7, wherein the evaluation map generating means statistically processes the point group data for every unit area, for the evaluating the road surface property.

9. The evaluation device of the road surface property according to claim 8, further comprising a displaying means that displays a result of evaluation obtained through statistical processing with the path shown on a map.

10. The evaluation device of the road surface property according to claim 6, wherein the model plane is calculated with a plurality of regions spaced apart in a direction of the predetermined road width in the unit area as a reference.

* * * * *